US010028955B2

(12) United States Patent
Kneissel et al.

(10) Patent No.: US 10,028,955 B2
(45) Date of Patent: Jul. 24, 2018

(54) FGFR INHIBITOR FOR USE IN THE TREATMENT OF HYPOPHOSPHATEMIC DISORDERS

(71) Applicant: Novartis AG, Base (CH)

(72) Inventors: Michaela Kneissel, Basel (CH); Vito Guagnano, Basel (CH); Diana Graus Porta, Basel (CH); Simon Wöhrle, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/272,633

(22) Filed: Sep. 22, 2016

(65) Prior Publication Data

US 2017/0007606 A1   Jan. 12, 2017

Related U.S. Application Data

(63) Continuation of application No. 14/388,978, filed as application No. PCT/EP2013/056811 on Mar. 29, 2013, now abandoned.

(60) Provisional application No. 61/617,889, filed on Mar. 30, 2012.

(51) Int. Cl.

| | |
|---|---|
| *A61K 31/506* | (2006.01) |
| *A61K 45/06* | (2006.01) |
| *A61K 33/42* | (2006.01) |
| *A61K 33/06* | (2006.01) |
| *A61K 38/17* | (2006.01) |
| *A61K 38/29* | (2006.01) |
| *A61K 31/59* | (2006.01) |

(52) U.S. Cl.
CPC ........... *A61K 31/506* (2013.01); *A61K 31/59* (2013.01); *A61K 33/06* (2013.01); *A61K 33/42* (2013.01); *A61K 38/1709* (2013.01); *A61K 38/29* (2013.01); *A61K 45/06* (2013.01)

(58) Field of Classification Search
CPC ........................... C07D 403/12; A61K 31/506
See application file for complete search history.

(56) References Cited

U.S. PATENT DOCUMENTS

2011/0045511 A1* 2/2011 Graus Porta ....... G01N 33/6872
435/7.92

FOREIGN PATENT DOCUMENTS

| EP | 1354949 | | 10/2003 | |
|---|---|---|---|---|
| EP | 1882475 | A1 | 1/2008 | |
| WO | WO 2006000420 | A1 * | 1/2006 | ........... C07D 239/48 |
| WO | WO2006000420 | A1 | 1/2006 | |
| WO | WO2009133101 | A1 | 11/2009 | |
| WO | WO2011051425 | A1 | 5/2011 | |
| WO | WO2011/075620 | A1 | 6/2011 | |
| WO | WO 2011071821 | A1 * | 6/2011 | ........... C07D 239/48 |
| WO | WO2011071821 | A1 | 6/2011 | |
| WO | 2013/087725 | | 6/2013 | |

OTHER PUBLICATIONS

S. H. Neau, Pharmaceutical Salts, in Water-Insoluble Drug Formulation 417, 429 (R. Liu ed., CRC Press, 2008).*
S. Badaway et al., Salt Selection for Pharmaceutical Compounds, in Preformulation in Solid Dosage Form Dev. 63 (M. Adeyeye ed., 2008).*
R.J. Bastin et al., Salt Selection and Optimization Procedures for Pharmaceutical New Chemical Entities, 4 Organic Process Res. Dev. 427 (2000).*
P.L. Gould, Salt Selection for Basic Drugs, 33 Int. J. Therapeutics 201, 217 (1986).*
K. R. Morris et al., An Integrated Approach to the Selection of Optimal Salt Form for a New Drug Candidate, 105 Int'l. J. Pharm. 209 (1994).*
K. Chow et al., Engineering of Pharmaceutical Materials: an Industrial Perspective, 97 J. Pharmaceutical Sciences, 2855-2877 (2008).*
E.M. Azous et al., 27 Pediatric Radiology, 75-78 (1997).*
P. Beighton et al., Journal of Medical Genetics, 572-576 (1989).*
Liu et al., "How Fibroblast Growth Factor 23 Works", J. Am. Soc. Nephrol., (2007),vol. 18, p. 1637-1647.
Khashayar Sakhaee, "Past-renal transplantation hypophosphatemia", Ped. Nephrol., (2010),vol. 25, p. 213-220.
White et al., "Mutations that Cause Osteoglophonic Dysplasia Define Novel Roles for FGFR1 in Bone Elongation", Am. J. Hum. Genet, (2005), vol. 76, p. 361-367.
Wohrle et al, "FGF Receptors Control Vitamin D and Phosphate Homeostasis by Mediating Renal FGF-23 Signaling and Regulating FGF-23 Expression in Bone", J. Bone Mine. Res., (2011), vol. 26, p. 2486-2497.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase", J. Med. Chem., (2011),vol. 54, p. 7066-7083.
Wöhrle, et.al., "Pharmacological inhibition of fibroblast growth factor (FGF) receptor signaling ameliorates FGF23-mediated hypophosphatemic rickets", Journal of Bone and Mineral Research, vol. 28, No. 4, pp. 800-911, Apr. 18, 2013.
Neau, "Pharmaceutical Salts", Water-Insoluble Drug Formulation, 2008 pp. 417-429.

(Continued)

*Primary Examiner* — Alexander R Pagano
(74) *Attorney, Agent, or Firm* — Goodwin Procter LLP (57) ABSTRACT

The present invention relates generally to 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt or solvate thereof or a pharmaceutical composition comprising 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt or solvate thereof for use in the treatment of X-linked hypophosphatemic rickets (XLH), autosomal dominant hypophosphatemic rickets (ADHR), autosomal recessive hypophosphatemic rickets (ARHR), tumor-induced osteomalacia, post-renal transplant hypophosphatemia, epidermal nevus syndrome, osteoglophonic dysplasia or McCune-Albright syndrome.

6 Claims, 9 Drawing Sheets

(56) References Cited

OTHER PUBLICATIONS

Badawy et al., "Salt Selection for Pharmaceutical Compounds", Preformulation in Solid Dosage Form Development, 2008, pp. 63-80.
Bastin et al., "Salt Selection and Optimisation Procedures for Pharmaceutical New Chemical Entities", Organic Process Research and Development, 2000, vol. 4, No. 5 , pp. 427-435.
Gould, "Salt Selection for basic drugs", International Journal of Pharmaceutics, 1986, vol. 33, pp. 201-217.
Morris et al., "An integrated approach to the selection of optimal salt form for a new drug candidate", International Journal of Pharmaceutics, 1994, vol. 105, pp. 209-217.
Chow et al., "Engineering of Pharmaceutical Materials: An Industrial Perspective", Journal of Pharmaceutical Sciences, 2008, vol. 97, No. 8, pp. 2855-2877.
Mosekilde L. "Primery hyperparathyroidism and the skeleton". Clin. Endocrinol(Oxf) Jul. 2008; 69(1):1-19, May 7, 2017.
Marsell R. et al. "Relation between fibroblast growth factor-23, body weight and bone mineral density in elderly men". Osteoporos. Int. Jul. 2009; 20(7):1167-1173,.

* cited by examiner

FGFR INHIBITOR FOR USE IN THE TREATMENT OF HYPOPHOSPHATEMIC DISORDERS

CROSS-REFERENCE TO RELATED APPLICATIONS

This application is a continuation patent application under 35 U.S.C. § 120 of U.S. patent application Ser. No. 14/388,978, filed on Sep. 29, 2014, now abandoned, which application is a U.S. national stage application under 35 U.S.C. § 371 of International Application No. PCT/EP2013/056811, filed on Mar. 29, 2013, which claims priority to and the benefit of U.S. patent application Ser. No. 61/617,889, filed on Mar. 30, 2012, each of which is incorporated by reference herein in its entirety.

FIELD OF THE INVENTION

The present invention relates generally to 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt or solvate thereof or a pharmaceutical composition comprising 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt or solvate thereof for use in the treatment of the fibroblast growth factor receptor mediated disorders.

BACKGROUND OF THE INVENTION

The fibroblast growth factor (FGF) family and their signaling receptors are associated with multiple biological activities (proliferation, survival, apoptosis, differentiation, motility) that govern key processes (development, angiogenesis, and metabolism) for the growth and maintenance of organisms from worms to humans. 22 distinct FGFs have been identified, all sharing a conserved 120-aminoacids core domain with 15-65% sequence identity. FGF23 is a critical, bone-derived mediator of phosphate homeostasis, which functions in the kidney to regulate vitamin D biosynthesis and renal absorption of phosphate. In kidney proximal tubule epithelial cells, FGF23 signaling controls expression of the vitamin D metabolizing enzymes CYP27B1 and CYP24A1, resulting in decreased biosynthesis and elevated turnover of the active vitamin D metabolite 1,25-dihydroxyvitamin D3 (1,25[OH]2D3). In addition, FGF23 impairs expression of the sodium-phosphate co-transporters NPT2A and NPT2C in the brush border membrane of proximal tubular cells, which mediate the re-absorption of urinary phosphate.

Excess levels or augmented function of FGF23 result in hypophosphatemia along with impaired biosynthesis of 1,25 (OH)2D3(vitamin D) and are associated with several hereditary hypophosphatemia disorders with skeletal abnormalities as a consequence of impaired bone mineralization, including X-linked hypophosphatemic rickets (XLH), autosomal dominant hypophosphatemic rickets (ADHR), and autosomal recessive hypophosphatemic rickets (ARHR). In addition, in rare cases secretion of FGF23 by tumor cells has been identified to cause hypophosphatemia resulting in tumor-induced osteomalacia (TIO). Elevated levels of FGF23 are also commonly observed in post-renal transplantation patients leading to servere hypophosphatemia. FGF23 plays a role in several other hypophosphatemic syndromes such as epidermal nevus syndrome, osteoglophonic dysplasia and McCune-Albright syndrome which have been associated with increased FGF23 levels. XLH and other FGF23-mediated hypophosphatemia diseases such as ADHR and ARHR commonly manifest clinically in early childhood with short stature and bowing deformities of the legs.

Current therapeutic approaches to these diseases are mainly limited to dietary vitamin D and phosphate supplementation. Although therapy improves growth and rickets in patients, correction is often limited and results in impaired post-pubertal height. Depending on the severity of disease, but owing to the persistence of FGF23 signaling—constituting a continuous counteractive force—administration of high doses of phosphate and vitamin D are often required for medical therapy of XLH and other FGF23-related hypophosphatemia diseases, necessitating close monitoring and dose adjustments to avoid toxicity risks such as abdominal pain and diarrhea or secondary hyperparathyroidism, hypercalcemia and ectopic calcifications.

Hence, there is a need for a reliable and efficacious medication for the treatment of the aforementioned disfiguring ailments and directly targeting pathological FGF23 signaling by blocking FGFR signal transduction might provide an advantageous therapeutic approach over the current standard of treatment.

SUMMARY OF THE INVENTION

It was now surprisingly found that the compound 3-(2,6-Dichloro-3,5-dimethoxy-phenyl)-1-{6-[4-(4-ethyl-piperazin-1-yl)-phenylamino]-pyrimidin-4-yl}-1-methyl-urea as depicted in formula I (described in example 145 of WO2006/000420), a highly selective, FGFR inhibitor also known as BGJ389, is clinically particularly active and can be used in the treatment of other fibroblast growth factor receptor mediated disorders.

In the first aspect, the present invention thus provides 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use in the treatment of X-linked hypophosphatemic rickets (XLH), autosomal dominant hypophosphatemic rickets (ADHR), autosomal recessive hypophosphatemic rickets (ARHR), tumor-induced osteomalacia, post-renal transplant hypophosphatemia, epidermal nevus syndrome, osteoglophonic dysplasia or McCune-Albright syndrome. Particularly the compound, its pharmaceutically acceptable salt or solvate, can be used in the treatment of X-linked hypophosphatemic rickets (XLH), autosomal dominant hypophosphatemic rickets (ADHR), autosomal recessive hypophosphatemic rickets (ARHR) or tumor-induced osteomalacia, post-renal transplant hypophosphatemia, Preferably, the 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt or solvate is administered to a patient in more than one dose.

When the compound 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof is used as defined above, the treatment should preferably last at least 8 weeks, optionally with an interruption. The time between two consecutive doses of the compound can be more than 24 hours, optionally 48 hours.

The compound of formula I can be further used in the treatment in combination with another FGFR inhibitor, phosphate, calcium, osteopontin (OPN), parathyroid hormone or its analogue (PTH), and/or vitamin D or vitamin D analogue, preferably in combination with phosphate, calcium and/or vitamin D or vitamin D analogue, particularly vitamin D or vitamin D analogue.

In a second aspect the invention provides a pharmaceutical composition comprising 3-(2,6-dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use as defined above.

Another aspect of the invention is 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use in increasing cortical bone volume or thickness when compared to a control or cortical bone volume or thickness before the beginning of the treatment.

Yet another aspect of the invention is 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use in gaining body weight in a patient that shows increased activity of FGF23 compared to control.

Further aspect of the invention is 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use in inhibiting FGF23 expression in bone or inhibiting FGF23 activity in bone.

DETAILED DESCRIPTION OF THE INVENTION

The fibroblast growth factor 23 (FGF23) is known. It is considered a member of the fibroblast growth factor family with broad biological activities. The sequence of the protein and/or the coding sequence of the protein can be retrieved from publicly available databases known in the art. Human FGF23 is also known in the art as ADHR; HYPF; HPDR2; PHPTC. FGF23 is the disease-causing factor in several hypophosphatemic conditions. Unexpectedly it was observed that pharmacological inhibition of FGFRs using the FGFR inhibitor 3-(2,6-Dichloro-3,5-dimethoxy-phenyl)-1-{6-[4-(4-ethyl-piperazin-1-yl)-phenylamino]-pyrimid-4-yl}-1-methyl-urea (BGJ398) counteracts pathological FGF23 signaling, thereby depicting a potential novel therapeutic approach for the treatment of FGF23-related hypophosphatemia disorders. We found that 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof can be very efficacious when used in the treatment of X-linked hypophosphatemic rickets (XLH), autosomal dominant hypophosphatemic rickets (ADHR), autosomal recessive hypophosphatemic rickets (ARHR), tumor-induced osteomalacia, post-renal transplant hypophosphatemia, epidermal nevus syndrome, osteoglophonic dysplasia or McCune-Albright syndrome. The compound can be especially useful for the treatment of X-linked hypophosphatemic rickets (XLH), autosomal dominant hypophosphatemic rickets (ADHR) or autosomal recessive hypophosphatemic rickets (ARHR), post-renal transplant hypophosphatemia, particularly X-linked hypophosphatemic rickets (XLH) and autosomal dominant hypophosphatemic rickets (ADHR) or autosomal recessive hypophosphatemic rickets (ARHR).

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "pharmaceutically acceptable salts" refers to salts that retain the biological effectiveness and properties of the compound when used according to this invention and, which typically are not biologically or otherwise undesirable. Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, oleate, oxalate, palmitate, pamoate, phosphate/hydrogen phosphate/dihydrogen phosphate, propionate, stearate, succinate, sulfosalicylate, tartrate, tosylate, trifluoroacetate salt or the like. Inorganic acids from which salts can be derived include, for example, hydrochloric acid, hydrobromic acid, sulfuric acid, nitric acid, phosphoric acid, and the like. In one embodiment, the pharmaceutically acceptable salt is monophosphoric acid salt (or phosphate) of the compound 3-(2,6-Dichloro-3,5-dimethoxy-phenyl)-1-{6-[4-(4-ethyl-piperazin-1-yl)-phenylamino]-pyrimid-4-yl}-1-methyl-urea, which can optionally be in anhydrous crystalline form. In specific embodiment, the salt of the compound is any salt or form disclosed in WO2011/071821. In one embodiment, 3-(2,6-Dichloro-3,5-dimethoxy-phenyl)-1-{6-[4-(4-ethyl-piperazin-1-yl)-phenylamino]-pyrimid-4-yl}-1-methyl-urea is in its free base form.

The term "solvate" refers to a molecular complex of the compound with one or more solvent molecules. Such solvent molecules are those commonly used in the pharmaceutical art, which are known to be innocuous to the compound, e.g., water, ethanol, and the like.

One of the N-Oxide of compound 3-(2,6-Dichloro-3,5-dimethoxy-phenyl)-1-{6-[4-(4-ethyl-piperazin-1-yl)-phenylamino]-pyrimid-4-yl}-1-methyl-urea has the following formula II (II)

Already a single effective dose of BGJ398 resulted in a strong increase in 1,25(OH)2D3 serum levels in both wild-type and Hyp mice at 7 h post-dosing of BGJ398. In addition, calcium and phosphate levels increased as well. These results indicate that pharmacological inhibition of FGFR is sufficient to counteract aberrant FGF23 signaling in a mammal. We found that single dose FGFR inhibitor already elicits its effect in terms of counteracting FGF23 activity and balancing calcium and phosphate levels in the body. Furthermore, long-term treatment with BGJ398 led to a complete normalization of both calcium and phosphate levels in Hyp mice. Therefore, in a preferred embodiment, BGJ398 or a pharmaceutically acceptable salt, N-oxide or solvate is administered to a patient in need thereof in more than one therapeutically effective dose. The term "a therapeutically effective dose" of the compound refers to an amount of the BGJ398 that will elicit the biological or medical response of a subject, for example, reduction or inhibition of kinase activity, or ameliorate symptoms, alleviate conditions, slow or delay disease progression, or prevent a disease, etc. The subject can be any mammal, including human. The therapeutically effective dose can be about 1-250 mg of BGJ398 for a subject of about 50-70 kg, or about 1-150 mg, for example at dose of 125 mg, or about 0.5-100 mg, or about 1-50 mg, or about 1-25 mg, or about 1-10 mg of BGJ398. The therapeutically effective dosage of the compound, whether alone or in the pharmaceutical composition, or in a combination with other active ingredients as explained hereinafter, is dependent on the species of the subject, the body weight, age and individual condition, the disorder or disease or the severity thereof being treated.

In another aspect of the invention is 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use in increasing cortical bone volume or thickness when compared to a control or cortical bone volume or thickness before the beginning of the treatment. The experiments that were conducted clearly show that the cortical bone volume increases from pathological values to indistinguishable with normal values when the subject is treated with BGJ398. In addition, cortex thickness was significantly increased.

It has been observed that administering of 3-(2,6-Dichloro-3,5-dimethoxy-phenyl)-1-{6-[4-(4-ethyl-piperazin-1-yl)-phenylamino]-pyrimid-4-yl}-1-methyl-urea leads to increased body weight gain in a patient that shows increased activity of FGF23 compared to control. A "control" refers to a value of FGF23 activity or expression in an individual, a number of subjects or population without the respective disease.

In a broader sense, one embodiment of the invention is 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof for use in inhibiting FGF23 expression in bone or inhibiting FGF23 activity in bone. "Expression" refers to the nucleic acids or amino acids generated when a gene is transcribed and translated. As an example, transcriptional activity can be assessed by any appropriate method, including for example, detecting the quantity of mRNA transcribed from the FGF23 gene or the quantity of cDNA produced from the reverse transcription of the mRNA transcribed from the gene or the quantity of the polypeptide or protein encoded by the gene. Alternatively any one of gene copy number, transcription, or translation can be determined using known techniques. For example, an amplification method such as PCR may be useful. By affecting the expression or activity of FGF23 in bone one can regulate its structure and growth, which is particularly useful in diseases that manifest themselves in irregular or unefficient growth and result in anomalies like for example, but not limited to, in rickets.

In order to reduce incidence of a likely side-effect of systemic FGFR inhibition, the dose can be administered intermittently in order to minimize the undesired secondary effect which may be harmful to the subject. Doses can be administered consecutively without interruptions, or starting first with a number of doses to achieve a steady state concentration in a patient in a need thereof and then modifying the time between the doses. Alternatively, the dosing can be adapted immediately after the first dose. The time between two consecutive doses of the compound can be more than 24 hours, optionally 48 hours or even a week. In a particular embodiment the dose is given repeatedly, optionally again with one, two, or three days between two consecutive doses, or only after a relapse.

In a preferred embodiment the compound 3-(2,6-Dichloro-3,5-dimethoxy-phenyl)-1-{6-[4-(4-ethyl-piperazin-1-yl)-phenylamino]-pyrimid-4-yl}-1-methyl-urea can be used in the treatment in combination with another FGFR inhibitor, phosphate, calcium, osteopontin (OPN), parathyroid hormone or its analogue (PTH), and/or vitamin D or vitamin D analogue, preferably in combination with phosphate, calcium and/or vitamin D or vitamin D analogue, particularly vitamin D or vitamin D analogue. The BGJ389 may be used in combination to advantage to bring about additive or even synergistic effects, but also to reduce the need of using higher doses of BGJ389 and consecutively to limit the risk of adverse effects. Phosphate can be used in any form which when taken orally or parenterally increases blood level of inorganic phosphorus (P), which may e.g. be measured in serum by ultraviolet method using for example kits from RANDOX Laboratories LTD, UK, and a clinical chemistry analyzer such as the HITACHI 717 analyzer (Roche Diagnostics). Calcium can also be in any form which eventually leads to, when taken, increased blood level of total calcium that may e.g. be measured in serum by ultraviolet method using kits for example from RANDOX Laboratories LTD and a clinical chemistry analyzer such as the HITACHI 717 analyzer. Osteopontin (OPN) referred to as secreted phosphoprotein 1, bone sialoprotein I or early T-lymphocyte activation 1, which is known. It is considered an extracellular structural protein involved in bone remodeling. Human osteopontin is known in the art as SPP1. Parathyroid hormone (PTH) or parathormone is known. It is considered a hormone involved in the regulation of the calcium level in blood. PTH analogue is a molecule that at least in part retains the activity of PTH and structurally resembles the complete PTH by being only shorter or has modified or additional substituents linked to the PTH backbone structure. Vitamin D is a known hormone responsible for calcium homeostasis and important for healthy bone phenotype. Its analogue is a structurally similar compound in that it mimics the chemical structure of Vitamin D and elicits similar pharmacological effect. An example of Vitamin D analogue is calcipotriol.

3-(2,6-dichloro-3,5-dimethoxy-phenyl)-1-{6-[4-(4-ethyl-piperazin-1-yl)-phenylamino]-pyrimid-4-yl}-1-methyl-urea, or a pharmaceutically acceptable salt, N-oxide or solvate thereof is formulated in a pharmaceutical composition which in turn can be used in any treatment as explained above. The pharmaceutical composition would normally comprise 3-(2,6-dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt, N-oxide or solvate thereof and one or more pharmaceutically acceptable excipients. The amount of the compound in the pharmaceutical composition is preferably therapeutically effective. Optionally, another FGFR inhibitor, phosphate, calcium, osteopontin (OPN), parathyroid hormone or its analogue (PTH), and/or vitamin D or vitamin D analogue, preferably in combination with phosphate, calcium and/or vitamin D or vitamin D analogue, particularly vitamin D or vitamin D analogue are added in the pharmaceutical composition according to the present invention. The pharmaceutical composition can be formulated for particular routes of administration such as oral administration, parenteral administration, and topical administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as compacting, tabletting, filtering, lyophilization, sterilization or the like. Excipient can be any conventional inert diluent, lubricating agent, buffering agent, binder, disintegration agent, sweetening agent, flavoring agent, as well as adjuvants, such as preservative, stabilizer, wetting agent, emulsifer, solvents, dispersion media, coating, surfactant, antioxidant, preservative (e.g. antibacterial agents, antifungal agents), isotonic agent, absorption delaying agent, salt, preservative, drug stabilizer, dye, and the like and combinations thereof.

Example 1

FGFR inhibitor treatment induces 1,25(OH)2D3 biosynthesis and alleviates hypocalcemia and hypophosphatemia in Hyp mice. Wild-type C57BL/6 and Hyp (B6.Cg-Phex-Hyp/J) mice were obtained from The Jackson Laboratory. Dmp1-null mice were generated by Feng et al. (J. Dent. Res. 2003; 82:776-780.). All mice were kept in cages under standard laboratory conditions. Mice were fed on a standard rodent diet with water ad libitum.

Wild-type or Hyp mice received a single oral dose of the FGFR inhibitor BGJ398 in its free base form (50 mg/kg) or vehicle and were studied 7 h after administration of the compound. BGJ398 or vehicle only (PEG-300/Glucose 5%, 2:1 mix) was administered by oral gavage. Mice were used at 5-7 weeks of age in the case of single dose administrations. Mice were anesthetized by isoflurane inhalation and blood was collected from the caval vein. Mice were sacrificed by exsanguination and kidney and tibial and femoral bones were obtained. Concentrations of BGJ398 in kidney at 7 h was also determined.

Kidneys were sampled, total RNA was isolated. For RNA isolation from mouse tibial and femoral bones, epiphyses were cut off and bone marrow was removed by centrifugation at 4° C. Tissue was homogenized using a Precellyis 24 bead homogenizer and RNA was extracted with TRIzol reagent. RNA was purified subsequently by chloroform extraction, isopropanol precipitation and RNeasy Mini kit. For kidney RNA, approximately 60 mg of tissue was homogenized in 1.5 ml RTL buffer (Qiagen) with a rotor-stator homogenizer and RNA was purified with the RNeasy Mini kit. Random hexamer primed cDNA was synthesized with 0.5-2 µg RNA and MultiScribe MuLV reverse transcriptase.

Gene expression was analyzed by quantitative real-time PCR (qPCR). TaqMan Probe-Based Gene Expression assays were used for expression analysis of mouse Cyp27b1 (Mm01165919), Cyp24a1 (Mm00487244) and Gapdh (4352339E). Sequences of primers and FAM/TAMRA-labeled probes (Microsynth) for the detection of mouse Fgf23 were 5'-TTTGGATCGCTTCACTTCAG (forward), 5'-GTGATGCTTCTGCGACAAGT (reverse) and 5'-CGCCAGTGGACGCTGGAGAA (probe). Quantitative real-time PCR was performed in an iQ5 Real-Time PCR Detection System using a qPCR core kit for probe assay and an equivalent of 40 or 80 ng RNA of each sample. The data were normalized to Gapdh expression.

Radiographs of femur and tibia were taken ex vivo using a high-resolution radiography system (Faxitron MX-20). µCT measurements were performed ex vivo using a Scanco vivaCT 40 system (voxel size 6 µm; high resolution). For cancellous and cortical bone analyses a fixed threshold of 200 was used to determine the mineralized bone fraction from 50 slices. A Gaussian filter was applied to remove noise ($\sigma=0.7$; support=1).

Serum was separated from whole blood using clot activator centrifugation tubes. 100 µl of serum were used for determination of phosphate and calcium levels using the VetScan diagnostic profiling system. Serum concentrations of 1,25(OH)2D3 were determined using a radio receptor assay kit. FGF23 serum levels were analyzed by an ELISA detecting intact FGF23 (Kainos).

Figure 1:
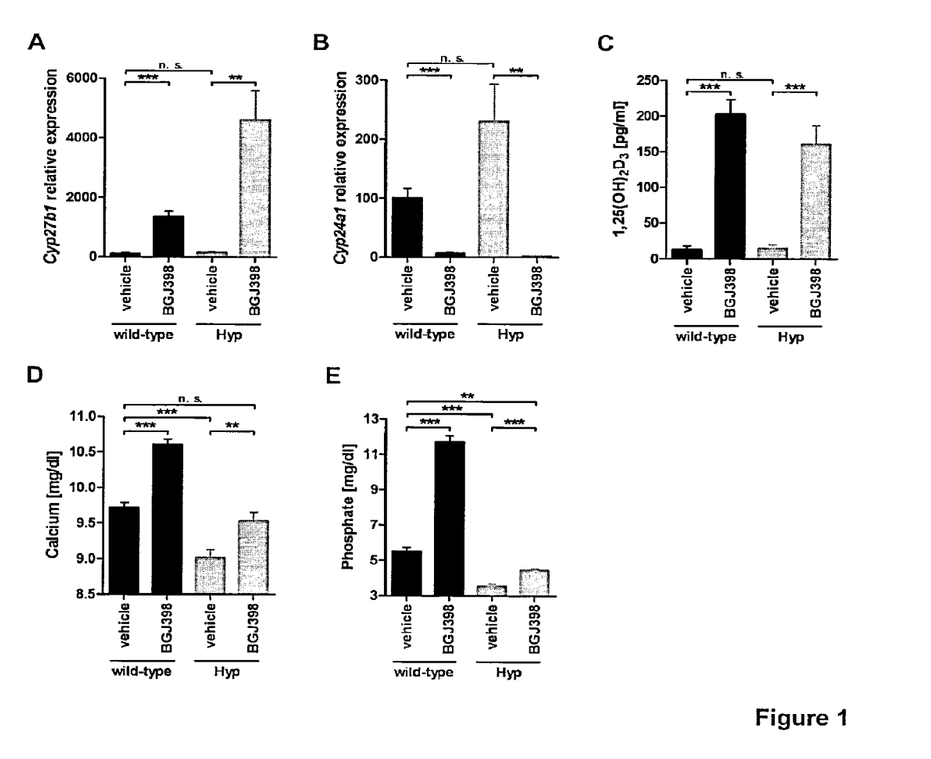
FIG. 1 FGFR inhibitor treatment induces 1,25(OH)2D3 biosynthesis and alleviates hypocalcemia and hypophosphatemia in Hyp mice. Regulation of the renal FGF23 target genes Cyp27b1 (A) and Cyp24a1 (B) upon FGFR inhibition for 7 h in vivo is shown. Data are shown as relative levels to the wild-type vehicle control group (relative expression of 100). (C) Serum 1,25(OH)2D3 levels of wild-type and Hyp mice treated as described in A and B were determined by radio receptor assay. Calcium (E) and phosphate (F) levels at 24 h post-administration in wild-type and Hyp mice treated with a single oral dose of BGJ398 (50 mg/kg) or vehicle. Phosphate and calcium levels were determined from serum. Data are given as average with SEM (n≥6). Data were compared by unpaired Student's t test; * $p<0.05$;  $p<0.01$; * $p<0.001$; n. s.: not significant.

FGF23 exerts its hypophosphatemic functions in part by transcriptional regulation of the 1,25(OH)2D3-metabolizing enzymes CYP27B1 and CYP24A1 in the kidney. We therefore monitored renal Cyp27b1 and Cyp24a1 expression upon single dose treatment with BGJ398 in Hyp mice and wild-type littermates. Despite elevated FGF23 levels present in Hyp mice, Cyp27b1 and Cyp24a1 expression and 1,25 (OH)2D3 serum levels in Hyp mice were not significantly different compared to wild-type mice (FIGS. 1A, B and C), potentially owing to adaption processes and in line with previous reports. In both wild-type and Hyp mice, treatment with BGJ398 for 7 h led to increased Cyp27b1 levels and an almost complete loss of Cyp24a1 expression (FIGS. 1A and B). Accordingly, this deregulation of the FGF23 target genes resulted in a strong increase in 1,25(OH)2D3 serum levels in both wild-type and Hyp mice at 7 h post-dosing of BGJ398 (FIG. 1C).

At 24 h post-dosing, single dose treatment with BGJ398 induced elevated serum calcium and phosphate levels in both wild-type and Hyp mice, thus alleviating the severe hypocalcemia and hypophosphatemia observed in control Hyp mice. With respect to calcium, serum levels of BGJ398-treated Hyp mice were indistinguishable from vehicle-treated wild-type mice (FIG. 1D), while serum phosphate concentrations in Hyp mice treated with the FGFR inhibitor were still significantly lower compared to serum levels of wild-type mice (FIG. 1E). Data in FIGS. 1 A and B is shown as relative levels to the wild-type control group (relative expression of 100) and are given as average with standard errors of the mean (SEM) (n≥6).

As explained, on the FIG. 1 regulation of the renal FGF23 target genes Cyp27b1 (A) and Cyp24a1 (FIG. 1B) upon FGFR inhibition in vivo is depicted. Also, (C) Serum 1,25(OH)2D3 levels of wild-type and Hyp mice treated as described in A and B were determined by radio receptor assay. In addition, Calcium (FIG. 1E) and (FIG. 1F) phosphate levels at 24 h post-administration in wild-type and Hyp mice treated with a single oral dose of BGJ398 (50 mg/kg) or vehicle are shown. All together this shows that FGFR inhibitor treatment induces 1,25(OH)2D3 biosynthesis and alleviates hypocalcemia and hypophosphatemia in Hyp mice. The results further indicate that pharmacological inhibition of FGFR is sufficient to counteract aberrant FGF23 signaling in Hyp mice.

Example 2

Figure 2:
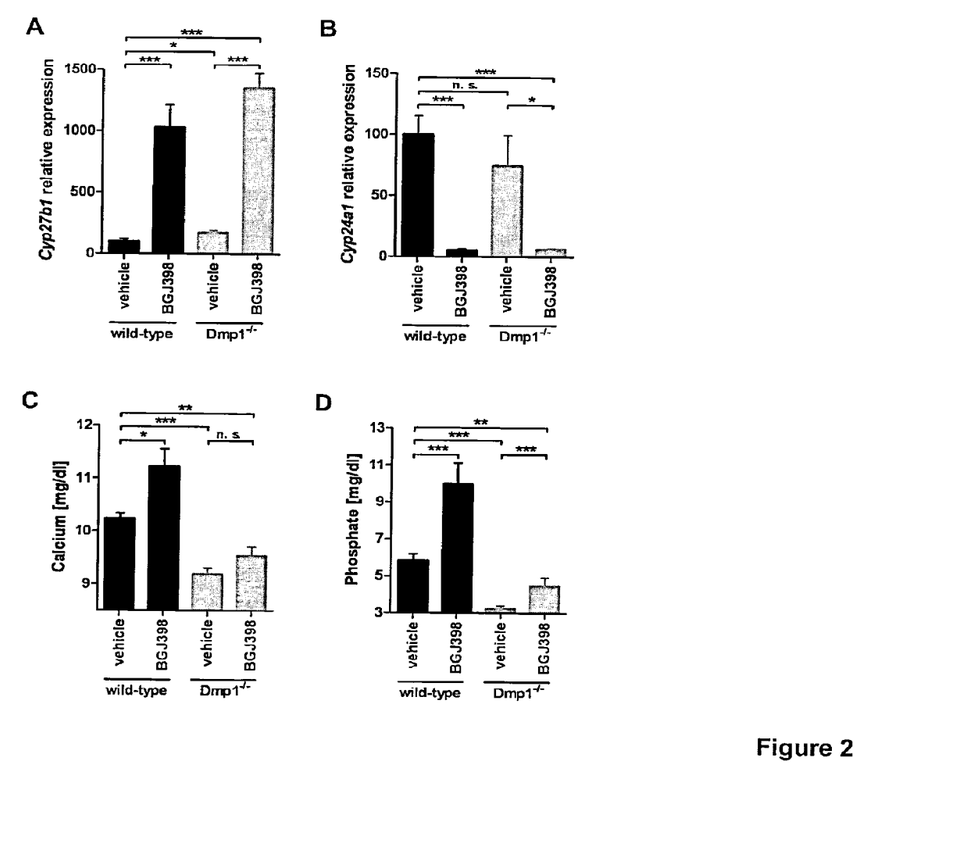
FIG. 2 FGFR inhibitor treatment modulates renal FGF23 target gene expression and alleviates hypocalcemia and hypophosphatemia in Dmp1-null mice. Regulation of the renal FGF23 target genes Cyp27b1 (A) and Cyp24a1 (B) upon FGFR inhibition in vivo. Data are shown as relative levels to the wild-type vehicle control group (relative expression of 100) and are given as average with standard errors of the mean (SEM) (n≥6). Effect of pharmacological FGFR inhibition on serum calcium (C) and phosphate (D) levels in wild-type and Dmp1-null mice. Data are shown as average with SEM (n≥6). Data were compared by unpaired Student's t test; * $p<0.05$;  $p<0.01$; * $p<0.001$; n. s.: not significant.

FGFR inhibitor treatment modulates renal FGF23 target gene expression and alleviates hypocalcemia and hypophosphatemia in Dmp1-null mice. Regulation of the renal FGF23 target genes Cyp27b1 (FIG. 2A) and Cyp24a1 (FIG. 2B) upon FGFR inhibition in vivo is shown on FIG. 2. In addition to our findings in the Phex-deficient Hyp model, we observed a similar regulation of renal Cyp27b1 and Cyp24a1 expression in Dmp1-null mice, another FGF23-related hypophosphatemia model (FIGS. 2A and B). Wild-type or Dmp1-null mice received a single oral dose of the FGFR inhibitor BGJ398 (50 mg/kg) or vehicle and were again studied 7 h after administration of the compound. As before, kidneys were sampled, total RNA was isolated and gene expression was analyzed by qPCR. Expression values were normalized to Gapdh mRNA copies. Data in A and B are shown as relative levels to the wild-type vehicle control group and are given as average with standard errors of the mean (SEM) (n≥6).

For analysis of calcium and phosphate levels mice received a single oral dose of the FGFR inhibitor BGJ398 (50 mg/kg) or vehicle and were studied 24 h post-administration. Phosphate and calcium levels were determined from serum. As for Hyp mice, pharmacological FGFR inhibition led to increased serum calcium and phosphate levels in Dmp1-null mice (FIGS. 2C and D, respectively). Data in FIG. 2 are shown as average with SEM (n≥6). Data were compared by unpaired Student's t test; * p<0.05;  p<0.01; * p<0.001; n. s.: not significant.

Example 3

Figure 3:
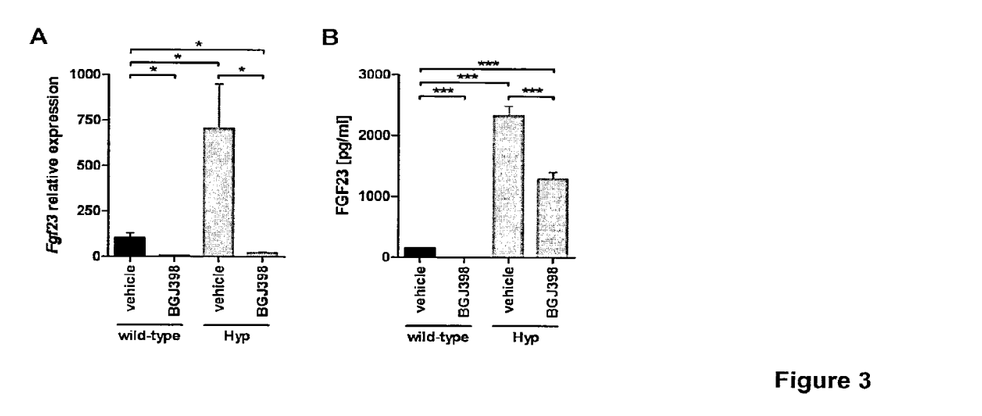
FIG. 3 shows FGFR-dependent signaling regulates FGF23 expression in bone. FGF23 bone mRNA (A) and serum (B) levels in wild-type and Hyp mice treated with BGJ398 for 7 h.

FIG. 3 shows FGFR-dependent signaling regulates FGF23 expression in bone. Besides the alleviation of the mineral ion deficiency in the two mouse models for FGF23-related hypophosphatemic rickets, we also noticed a repressive effect of FGFR inhibitor treatment on FGF23 levels in BGJ398-treated Hyp mice. Mice received a single oral dose of the FGFR inhibitor BGJ398 (50 mg/kg) or vehicle and were studied 7 h post-administration. FGF23 bone mRNA (FIG. 3A) and serum (FIG. 3B) levels in wild-type and Hyp mice treated with BGJ398 were determined. At 7 h post-dosing of BGJ398 FGF23 expression in bone of both Hyp and wild-type mice was almost abolished (FIG. 2A). The transcriptional repression of FGF23 resulted in undetectable serum FGF23 levels in wild-type mice, while the pathological high FGF23 levels in Hyp mice were reduced by approximately 50% (FIG. 3B). mRNA expression is shown on the figure as relative levels to the wild-type vehicle control group (relative levels of 100) and are given as average with SEM (n≥7). FGF23 mRNA expression values were normalized to Gapdh mRNA copies. Data were compared by unpaired Student's t test; * p<0.05;  p<0.01; * p<0.001.

Example 4

Figure 4:
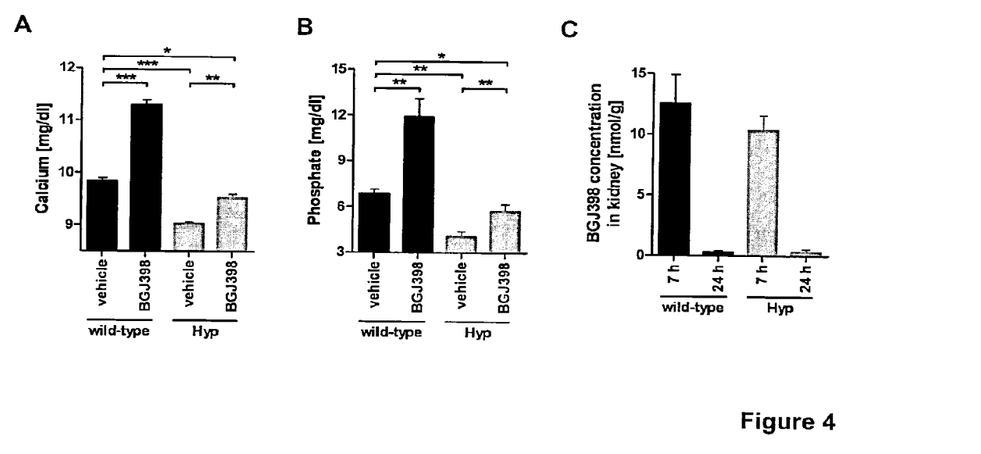
FIG. 4 shows that FGFR inhibitor treatment leads to a persistent increase of calcium and phosphate serum levels. Determination of Calcium (A) and phosphate (B) levels from serum in Wild-type or Hyp mice 48 h after administration of the compound of formula I. (C) Compound concentration in the kidney after 7 h and 24 h of treatment.

FIG. 4 clearly shows that FGFR inhibitor treatment leads to a persistent increase of calcium and phosphate serum levels. Similarly to example 1, wild-type or Hyp mice received a single oral dose of the FGFR inhibitor BGJ398 or vehicle and were studied 48 h after administration of the compound. Calcium (FIG. 4A) and phosphate (FIG. 4B) levels were determined from serum. Data are shown as average with SEM (n≥3). Data were compared by unpaired Student's t test; * p<0.05;  p<0.01; * p<0.001; n. s.: not significant. (C) BGJ398 concentrations in kidney at 7 h and 24 h post-administration. Values are given as average with SEM (n≥5).

Example 5

Figure 5:
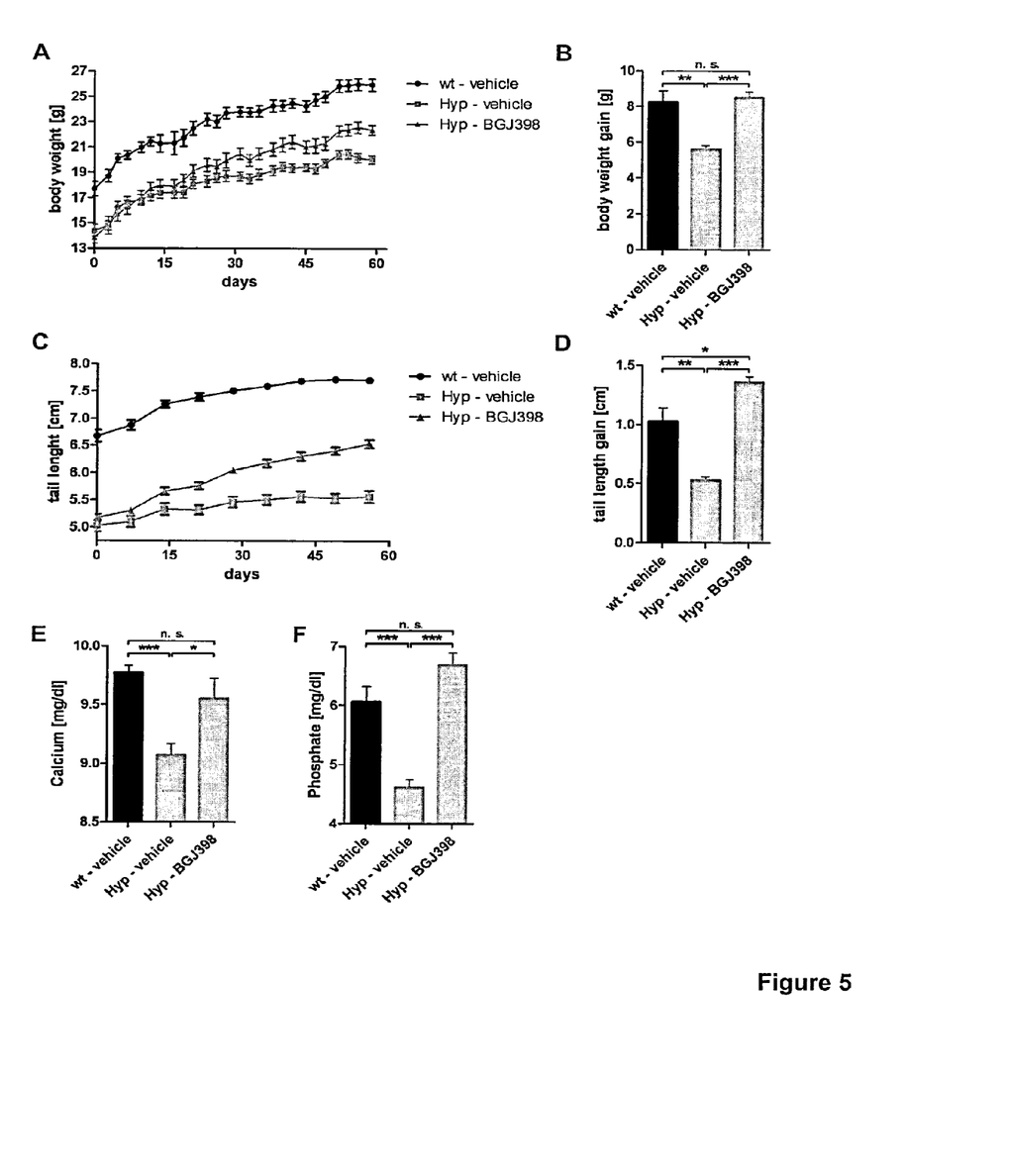
FIG. 5 Long-term FGFR inhibition enhances body weight and tail length development and restores mineral ion homeostasis in Hyp mice. Wild-type or Hyp mice were treated with the FGFR inhibitor BGJ398 (50 mg/kg) or vehicle 3 qw for 56 days and body weight (A) and tail length (C) development was monitored. Total body weight (B) and tail length gain (D) over the course of the treatment. Calcium (E) and phosphate (F) and levels at the end of the 8 week treatment were determined from serum 24 h after the last administration. Data are shown as average with SEM (n≥6). Data were compared by unpaired Student's t test; * $p<0.05$;  $p<0.01$; * $p<0.001$; n. s.: not significant.

Long-term FGFR inhibition enhances body weight and tail length development and restores mineral ion homeostasis in Hyp mice. A long-term treatment studies was performed to monitor a potential amelioration of the rickets-like bone phenotypes of the Hyp mouse model. Treatments were performed over a course of 8 weeks. Owing to the persistence of elevated calcium and phosphate levels—extending beyond the clearance of BGJ398 from the kidney (FIG. 4)—mice were treated three times weekly (3 qw) with BGJ398 (50 mg/kg body weight) or vehicle for 56 days and analyzed similarly as explained above. FIG. 5 shows body weight (FIG. 5A) and tail length (FIG. 5C) development as monitored. Total body weight (FIG. 5B) and tail length gain (FIG. 5D) over the course of the treatment are depicted in FIG. 5 as well. Calcium (FIG. 5E) and phosphate (FIG. 5F) levels at the end of the 8 week treatment were determined from serum 24 h after the last administration and are shown in FIG. 5. Data are shown as average with SEM (n≥6). Data were compared by unpaired Student's t test; * p<0.05;  p<0.01; * p<0.001; n. s.: not significant.

Compared to wild-type littermates, Hyp mice displayed a reduced body weight at 5 weeks of age, when the treatments were started. During the course of treatment, pharmacological FGFR inhibition in Hyp mice led to a stronger increase in body weight compared to the vehicle control group (FIG. 5A). Overall, the total body weight gain in BGJ398-treated Hyp mice was similar to vehicle-treated wild-type mice (FIG. 5B). A shorter tail is a pronounced feature of the hypophosphatemic rickets phenotype of Hyp mice, reflecting the impaired bone formation. Therefore, we monitored the tail length development during the 8 weeks of treatment and found that BGJ398-treated Hyp mice displayed a much stronger increase in tail length compared to control Hyp mice (FIG. 5C). Moreover, the tail length gain in Hyp mice treated with the FGFR inhibitor was also significantly higher compared to vehicle-treated wild-type littermates (FIG. 5D). To examine the effect of continuous FGFR inhibition on phosphate and calcium homeostasis in Hyp mice, we analyzed serum calcium and phosphate concentrations at the end of the 8 week study. We found that in contrast to single dose FGFR inhibitor administration (FIGS. 1D and E), long-term treatment with BGJ398 led to a complete normalization of both calcium and phosphate levels in Hyp mice (FIGS. 5E and F).

Example 6

Figure 6:
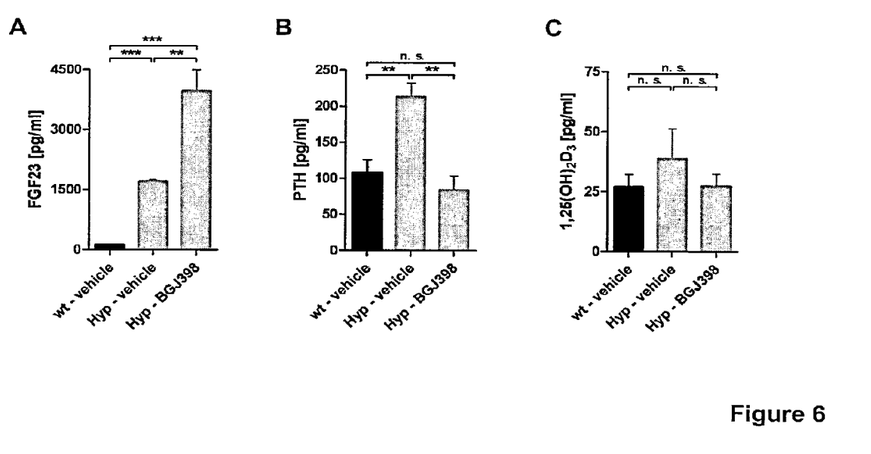
FIG. 6 Serum levels of FGF23, parathyroid hormone (PTH) and 1,25(OH)2D3 after long-term FGFR inhibition with BGJ398. Wild-type or Hyp mice were treated with the FGFR inhibitor BGJ398 (50 mg/kg) or vehicle 3 qw for 56 days and FGF23 (A), PTH (B) and 1,25(OH)2D3 (C) levels were determined from serum at 24 h after the last dosing. Data are shown as average with SEM (n≥4). Data were compared by unpaired Student's t test; * $p<0.05$;  $p<0.01$; * $p<0.001$; n. s.: not significant.

FIG. 6 shows serum levels of FGF23, parathyroid hormone (PTH) and 1,25(OH)2D3 after long-term FGFR inhibition with BGJ398. Wild-type or Hyp mice were treated again with the FGFR inhibitor BGJ398 (50 mg/kg) or vehicle 3 qw for 56 days and FGF23 (FIG. 6A), parathyroid hormone (PTH) (FIG. 6B) and 1,25(OH)2D3 (FIG. 6C) levels were determined from serum at 24 h after the last dosing. PTH values were determined by separating the serum from whole blood using clot activator centrifugation tubes (Sarstedt). 20 µl of serum were used for determination PTH levels using a mouse PTH ELISA (Immutopics). Data were compared by unpaired Student's t test; * p<0.05;  p<0.01; * p<0.001; n. s.: not significant.

Despite the transient repressive effect of FGFR inhibition on FGF23 expression (see FIG. 3), long-term treatment with BGJ398 led to a further increase of FGF23 serum concentrations in Hyp mice (FIG. 6A) which was accompanied by a normalization of PTH levels (FIG. 6B), while 1,25(OH) 2D3 was not significantly different among the treatment groups (FIG. 6C).

Example 7

Figure 7:
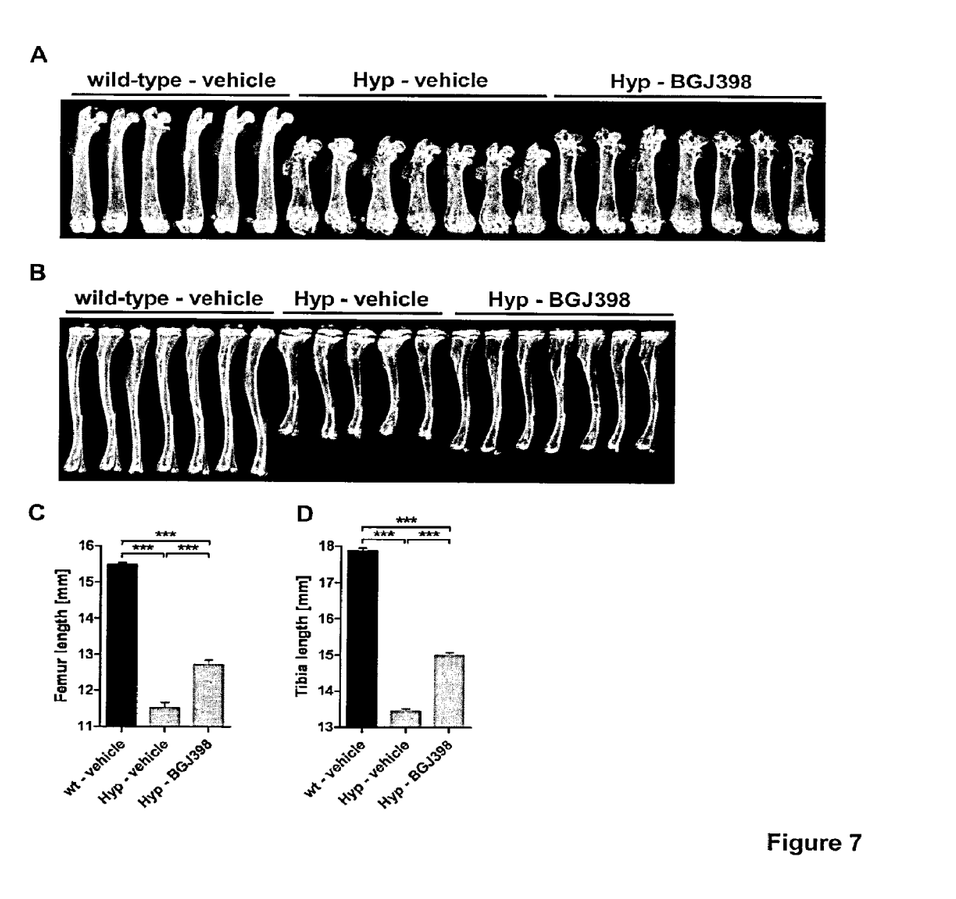
FIG. 7 Long-term FGFR inhibition enhances growth of long bones in Hyp mice. Radiographs of femur (A) and tibia (B) from wild-type or Hyp mice treated with the FGFR inhibitor BGJ398 (50 mg/kg) or vehicle 3 qw for 56 days. Quantification of femoral (C) and tibial (D) length. Data are shown as average with SEM (n≥6). Data were compared by unpaired Student's t test; * $p<0.05$;  $p<0.01$; * $p<0.001$; n. s.: not significant.

As shown on FIG. 7 long-term FGFR inhibition enhances growth of long bones in Hyp mice. Taken together, these above results illustrate the beneficial effect of pharmacological FGFR inhibition in the context of aberrant FGF23 signaling and indicate a potential alleviation of the bone formation deficiency of Hyp mice. We therefore analyzed the effect of long-term (8 weeks) FGFR inhibition on longitudinal growth of femur and tibia by radiography and found that BGJ398-treated Hyp mice displayed significant elongation of both femur (FIGS. 7 A and C) and tibia (FIGS. 7B and D) compared to the vehicle treated control group. FGFR inhibition did partially alleviate the widening of both femoral and tibial growth plate areas, which is typically observed in rickets (FIGS. 7A and B). On FIG. 7.: Radiographs of femur (FIG. 7A) and tibia (FIG. 7B) from wild-type or Hyp mice treated with the FGFR inhibitor BGJ398 (50 mg/kg) or vehicle 3 qw for 56 days. Quantification of femoral (FIG. 7C) and tibial (FIG. 7D) length. Data are shown as average with SEM (n≥6). Data were compared by unpaired Student's t test; * p<0.05;  p<0.01; * p<0.001; n. s.: not significant.

Example 8

Figure 8:
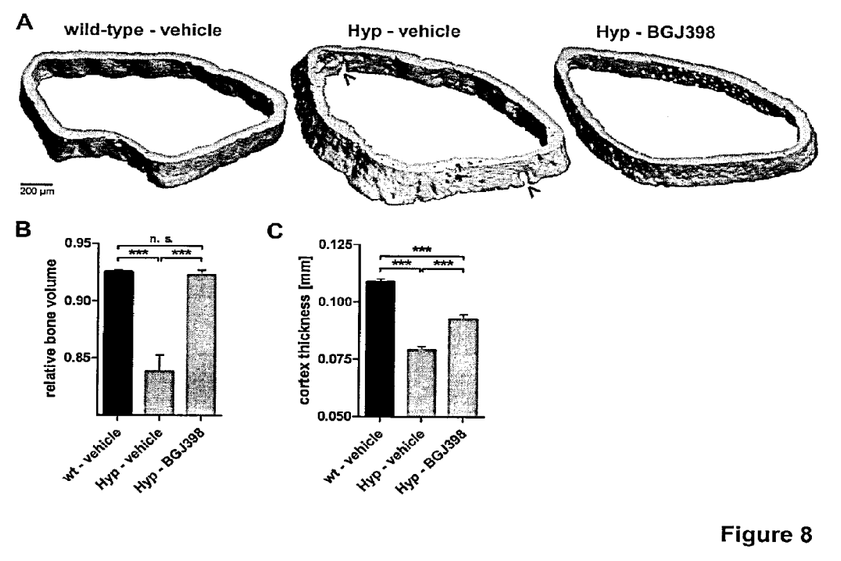
FIG. 8 Long-term FGFR inhibition improves cortex integrity in femoral bone of Hyp mice. (A) Micro-CT scans of femoral cortex (sub growth plate area) from wild-type or Hyp mice treated with the FGFR inhibitor BGJ398 (50 mg/kg) or vehicle 3 qw for 56 days. Quantification of relative cortical bone volume (B) and average cortex thickness (C). Data are shown as average with SEM (n≥6). Data were compared by unpaired Student's t test; * $p<0.05$;  $p<0.01$; * $p<0.001$; n. s.: not significant.

Long-term FGFR inhibition improves cortex integrity in femoral bone of Hyp mice. To determine the effect of FGFR inhibitor treatment on bone structure in more detail, we performed microcomputed tomography (CT) analyses of the femoral cortex (sub growth plate area) from wild-type or Hyp mice treated with the FGFR inhibitor BGJ398 (50 mg/kg) or vehicle 3 qw for 56 days (FIG. 8A). Further relative cortical bone volume was quantified (FIG. 8B) and average cortex thickness determined (FIG. 8C). This analysis revealed impaired mineralization of the cortical bone area in Hyp mice, apparent by gaps and holes within the Hyp femoral cortex structure (FIG. 8A, indicated by arrowheads). Compared to wild-type mice, vehicle-treated Hyp mice displayed reduced relative bone volume in the cortical bone area (FIG. 8B) and a decreased average cortex thickness (FIG. 8C). In contrast, cortex of BGJ398-treated Hyp mice appeared intact (FIG. 8A), relative cortical bone volume was indistinguishable from wild-type mice (FIG. 8B) and cortex thickness was significantly increased compared to vehicle-treated Hyp mice (FIG. 8C).

Hence, the analyses revealed a beneficial effect of FGFR inhibition on longitudinal growth and structural integrity of bone in Hyp mice.

Example 9

Figure 9:
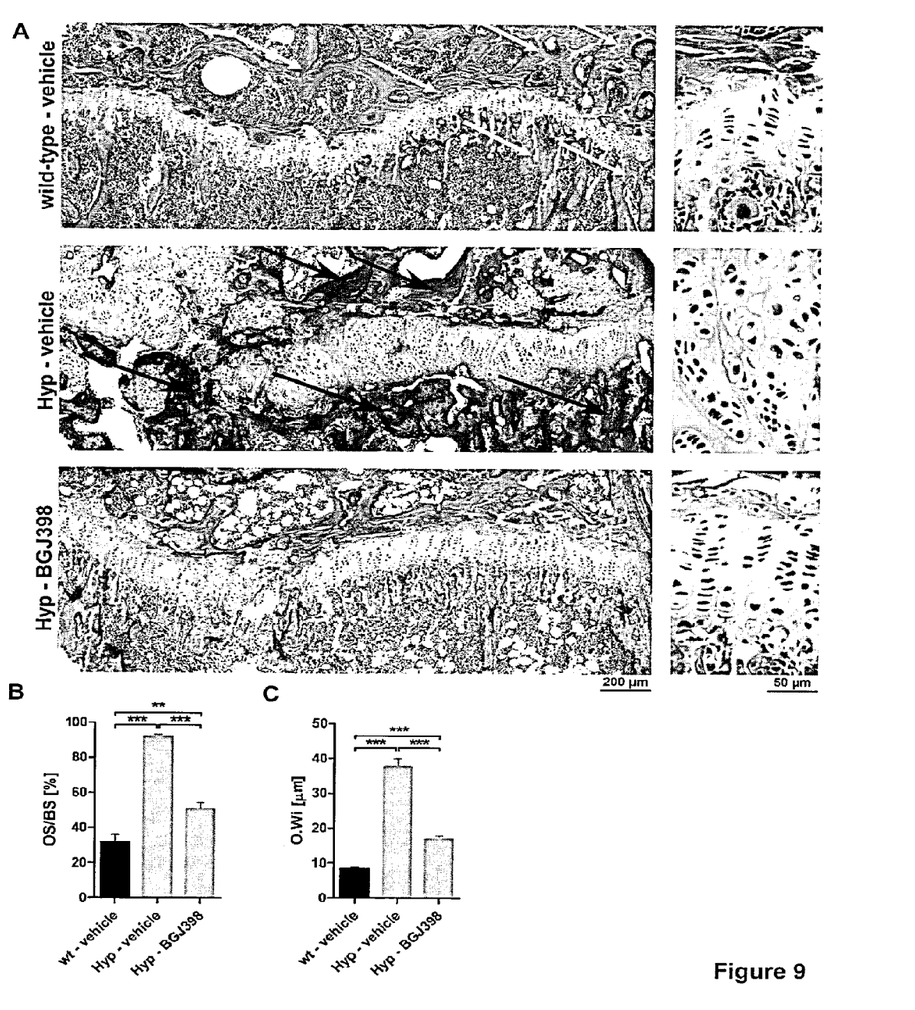
FIG. 9 shows Goldner staining of tibial sections from wild-type or Hyp mice treated with the FGFR inhibitor BGJ398 (50 mg/kg) or vehicle 3 qw for 56 days (A). Mineralized tissue is indicated by white arrows, unmineralized osteoid is indicated by black arrows, (B) Osteoid surface/bone surface and osteoid width (C) determined by histomorphometry in the tibial epiphysis of wild-type or Hyp mice treated with BGJ398 (50 mg/kg) or vehicle 3 qw for 56 days. Data are shown as average with SEM (n≥6). Data were compared by unpaired Student's t test; * $p<0.05$;  $p<0.01$; * $p<0.001$.

Long-term treatment with BGJ398 restores growth plate organization Hyp mice. we also found an ameliorative effect of BGJ398-treatment on growth plate organization in Hyp mice in tibial histological sections (FIG. 9A). FIG. 9 shows Goldner staining of tibial sections from wild-type or Hyp mice treated with the FGFR inhibitor BGJ398 (50 mg/kg) or vehicle 3 qw for 56 days (FIG. 9A). Mineralized tissue is indicated by white arrows, unmineralized osteoid is visualized by dark grey (indicated by black arrows). Growth plate structure is shown by light grey staining in the central part of the sections (FIG. 9B). Osteoid surface/bone surface and osteoid width (FIG. 9C) determined by histomorphometry in the tibial epiphysis of wild-type or Hyp mice treated with BGJ398 (50 mg/kg) or vehicle 3 qw for 56 days. Data are shown as average with SEM (n≥6). Data were compared by unpaired Student's t test; * p<0.05;  p<0.01; * p<0.001. In vehicle-treated Hyp mice the columnar organization and directional growth of chondrocytes was disturbed in contrast to the highly ordered structure in wild-type mice. In addition, mineralization was impaired in control Hyp mice, as indicated by the abundance of unmineralized osteoid. In BGJ398-treated Hyp mice, however, we observed a striking re-organization of the growth plate area (FIG. 9A, left panels), and a re-formation of the columnar stacks of chondrocytes along with an increased height of the proliferative zone (FIG. 9B, right panels). Additionally, we noticed enhanced mineralization in the epiphyseal bone area adjacent to the growth plate as well as the formation of primary spongiosa in the metaphyseal sub-growth plate area, which was almost absent in vehicle-treated Hyp mice. Likewise, histomorphometric analysis revealed an attenuation of the increased OS/BS ratio in Hyp mice in upon FGFR inhibition (FIG. 9B) and a strong reduction of osteoid width within the epiphyseal, metaphyseal and cortical bone compartments (FIG. 9C).

In summary, our data indicate that pharmacological inhibition of FGFRs is sufficient to inhibit aberrant FGF23-signaling and to alleviate the hypophosphatemic rickets phenotype of XLH and potentially other FGF23-related hypophosphatemia diseases, such as ARHR. In particular, the complete normalization of phosphate and calcium levels in Hyp mice upon continuous dosing of the FGFR inhibitor BGJ398 and the re-organization of the growth plate area in rickets-resembling bone are promising, since this constitutes a prerequisite for a potential reversion of the hypophosphatemic rickets phenotype.

The invention claimed is:

1. A method of treating a disease selected from the group consisting of post-renal transplant hypophosphatemia, epidermal nevus syndrome, osteoglophonic dysplasia and McCune-Albright syndrome with a therapeutically effective amount of 3-(2,6-Dichloro-3,5-dimethoxy-phenyl)-1-{6-[4-(4-ethyl-piperazin-1-yl)-phenylamino]-pyrimid-4-yl}-1-methyl-urea or a pharmaceutically acceptable salt thereof.

2. The method of treatment according to claim 1 further comprising a treatment that lasts at least 8 weeks and the dose is about 1-50 mg of 3-(2,6-Dichloro-3,5-dimethoxy-phenyl)-1-{6-[4-(4-ethyl-piperazin-1-yl)-phenylamino]-pyrimid-4-yl}-1-methyl-urea monophosphoric acid salt.

3. The method according to claim 2 wherein the dose is about 1-25 mg.

4. The method according to claim 1 wherein said 3-(2,6-Dichloro-3,5-dimethoxy-phenyl)-1-{6-[4-(4-ethyl-piperazin-1-yl)-phenylamino]-pyrimid-4-yl}-1-methyl-urea is in the form of monophosphoric acid salt and is used in combination with another FGFR inhibitor, phosphate, calcium, osteopontin (OPN), parathyroid hormone or its analogue (PTH), vitamin D or vitamin D analogue.

5. The method of claim 1, wherein 3-(2,6-Dichloro-3,5-dimethoxy-phenyl)-1-{6-[4-(4-ethyl-piperazin-1-yl)-phenylamino]-pyrimid-4-yl}-1-methyl-urea is in the form of monophosphoric acid salt.

6. The method of claim 1, wherein 3-(2,6-Dichloro-3,5-dimethoxy-phenyl)-1-{6-[4-(4-ethyl-piperazin-1-yl)-phenylamino]-pyrimid-4-yl}-1-methyl-urea is in the form of free base.

* * * * *